United States Patent
Kobayashi et al.

(10) Patent No.: US 9,448,153 B2
(45) Date of Patent: Sep. 20, 2016

(54) SEMICONDUCTOR ANALYSIS MICROCHIP AND METHOD OF MANUFACTURING THE SAME

(71) Applicant: KABUSHIKI KAISHA TOSHIBA, Minato-ku, Tokyo (JP)

(72) Inventors: Kentaro Kobayashi, Tokyo (JP); Hideto Furuyama, Yokohama (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 0 days.

(21) Appl. No.: 14/012,599

(22) Filed: Aug. 28, 2013

(65) Prior Publication Data

US 2014/0252505 A1 Sep. 11, 2014

(30) Foreign Application Priority Data

Mar. 7, 2013 (JP) .................. 2013-045393

(51) Int. Cl.
| | |
|---|---|
| *H01L 27/14* | (2006.01) |
| *G01N 15/06* | (2006.01) |
| *G01N 33/487* | (2006.01) |
| *B01L 3/00* | (2006.01) |
| *G01N 15/00* | (2006.01) |
| *G01N 27/447* | (2006.01) |

(52) U.S. Cl.
CPC ..... *G01N 15/0606* (2013.01); *B01L 3/502707* (2013.01); *B01L 3/502753* (2013.01); *G01N 15/0656* (2013.01); *G01N 33/48721* (2013.01); *B01L 2300/0681* (2013.01); *B01L 2400/0421* (2013.01); *B01L 2400/086* (2013.01); *G01N 27/44791* (2013.01); *G01N 2015/0065* (2013.01)

(58) Field of Classification Search
CPC .................. B01L 3/502707; B01L 2200/0647
USPC ........................................................ 257/414
See application file for complete search history.

(56) References Cited

U.S. PATENT DOCUMENTS

| | | |
|---|---|---|
| 6,537,437 B1 | 3/2003 | Galambos et al. |
| 7,297,151 B2 | 11/2007 | Boecker et al. |
| 7,390,388 B2 | 6/2008 | Childers et al. |
| 7,604,592 B2 | 10/2009 | Freeman et al. |
| 7,883,665 B2 | 2/2011 | Aizenberg et al. |
| 7,977,122 B2 | 7/2011 | Sandoz et al. |

(Continued)

FOREIGN PATENT DOCUMENTS

| | | |
|---|---|---|
| CN | 1720438 A | 1/2006 |
| CN | 103718029 A | 4/2014 |

(Continued)

OTHER PUBLICATIONS

NPL Machine Translation 2008-39541.*

(Continued)

*Primary Examiner* — Trung Q Dang
*Assistant Examiner* — Patricia Reddington
(74) *Attorney, Agent, or Firm* — Holtz, Holtz & Volek PC

(57) ABSTRACT

According to one embodiment, a semiconductor analysis microchip configured to detect a fine particle in a sample liquid, including a semiconductor substrate, a first flow channel provided in the semiconductor substrate, to which the sample liquid is introduced, and a pore provided in the first flow channel and configured to pass the fine particle in the sample liquid.

9 Claims, 13 Drawing Sheets

(56) References Cited

U.S. PATENT DOCUMENTS

| | | | |
|---|---|---|---|
| 8,158,410 B2 | 4/2012 | Tang et al. | |
| 8,182,635 B2 | 5/2012 | Ayliffe et al. | |
| 8,409,523 B2 | 4/2013 | Mendel-Hartvig et al. | |
| 8,608,891 B2 | 12/2013 | Ayliffe et al. | |
| 8,722,423 B2 | 5/2014 | Bergman et al. | |
| 8,759,115 B2 | 6/2014 | Ohman et al. | |
| 8,821,812 B2 | 9/2014 | Ohman et al. | |
| 8,974,749 B2 | 3/2015 | Bergman et al. | |
| 2003/0040173 A1* | 2/2003 | Fonash | B01J 19/0093 438/622 |
| 2003/0119034 A1 | 6/2003 | Kang et al. | |
| 2004/0053422 A1 | 3/2004 | Chan et al. | |
| 2004/0144658 A1 | 7/2004 | Flory | |
| 2005/0019784 A1 | 1/2005 | Su et al. | |
| 2005/0042766 A1 | 2/2005 | Ohman et al. | |
| 2006/0000772 A1 | 1/2006 | Sano et al. | |
| 2006/0035386 A1 | 2/2006 | Hattori et al. | |
| 2006/0073489 A1 | 4/2006 | Li et al. | |
| 2007/0242560 A1 | 10/2007 | Norikane et al. | |
| 2008/0278728 A1 | 11/2008 | Tetz et al. | |
| 2008/0311375 A1 | 12/2008 | Harnack et al. | |
| 2009/0136958 A1 | 5/2009 | Gershow et al. | |
| 2009/0194429 A1 | 8/2009 | Hibbs et al. | |
| 2009/0208920 A1 | 8/2009 | Öhman et al. | |
| 2011/0291026 A1* | 12/2011 | Renna et al. | 250/458.1 |
| 2012/0043202 A1 | 2/2012 | Miyamura et al. | |
| 2012/0228730 A1 | 9/2012 | Akiyama et al. | |
| 2012/0258479 A1 | 10/2012 | Ding et al. | |
| 2012/0292496 A1 | 11/2012 | Escobedo et al. | |
| 2013/0065777 A1 | 3/2013 | Altug et al. | |
| 2014/0158540 A1 | 6/2014 | Ohura | |

FOREIGN PATENT DOCUMENTS

| | | |
|---|---|---|
| JP | 2001088096 A | 4/2001 |
| JP | 2003315349 A | 11/2003 |
| JP | 2004219370 A | 8/2004 |
| JP | 2004-317340 A | 11/2004 |
| JP | 2004-325304 A | 11/2004 |
| JP | 2004354364 A | 12/2004 |
| JP | 2005098818 A | 4/2005 |
| JP | 2005230647 A | 9/2005 |
| JP | 2005532151 A | 10/2005 |
| JP | 2006-090910 A | 4/2006 |
| JP | 2006130400 A | 5/2006 |
| JP | 2007090135 A | 4/2007 |
| JP | 2007170840 A | 7/2007 |
| JP | 2008-039541 A | 2/2008 |
| JP | 2009-264904 A | 11/2009 |
| JP | 4366327 B2 | 11/2009 |
| JP | 2009541737 A | 11/2009 |
| JP | 2010-185703 A | 8/2010 |
| JP | 2010-187664 A | 9/2010 |
| JP | 2012255810 A | 12/2012 |
| JP | 2013036865 A | 2/2013 |
| JP | 2014521956 A | 8/2014 |
| TW | 200415346 A | 8/2004 |
| TW | 200528389 A | 9/2005 |
| TW | 200638037 A | 11/2006 |
| TW | 200712494 A | 4/2007 |
| WO | 2009126257 A1 | 10/2009 |
| WO | 2013016486 A1 | 1/2013 |
| WO | 2013137209 A1 | 9/2013 |

OTHER PUBLICATIONS

NPL Machine Translation JP 2008-39541.*

U.S. Appl. No. 14/011,640, First Named Inventor: Kentaro Kobayashi, Title: "Semiconductor Micro Analysis Chip and Sample Liquid Flowing Method", filed Aug. 27, 2013.

U.S. Appl. No. 14/011,666, First Named Inventor: Sadato Hongo, Title: "Sample Detection Apparatus and Detection Method", filed Aug. 27, 2013.

U.S. Appl. No. 14/012,566, First Named Inventor: Kentaro Kobayashi, Title: "Semiconductor Micro Analysis Chip and Manufacturing Method Thereof", filed Aug. 28, 2013.

U.S. Appl. No. 14/198,425, First Named Inventor: Hiroko Miki, Title: "Semiconductor Micro-Analysis Chip and Method of Manufacturing the Same", filed Mar. 5, 2014.

Japanese Office Action (and English translation thereof) dated Jun. 30, 2015, issued in counterpart Japanese Application No. 2013-045393.

* cited by examiner

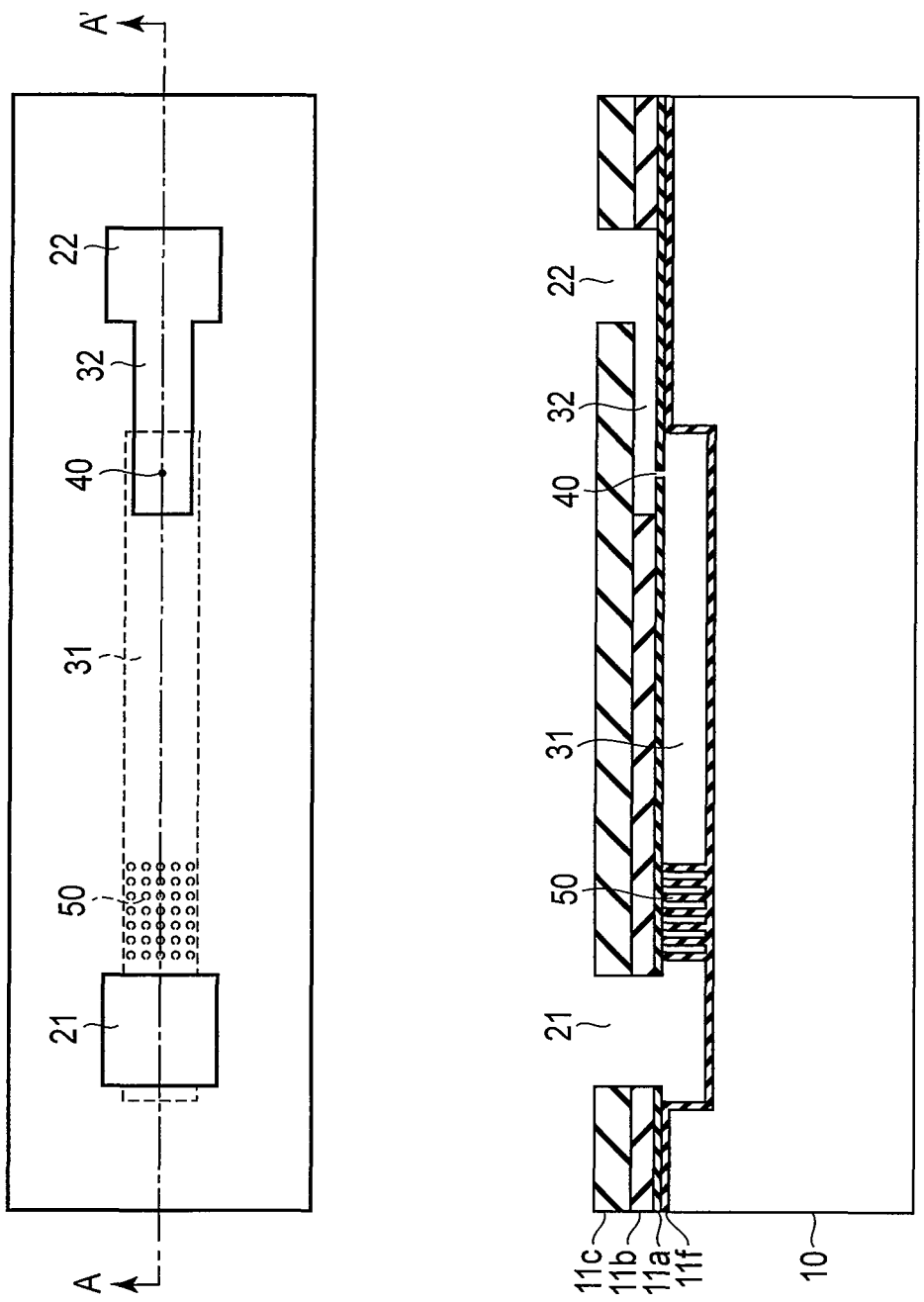

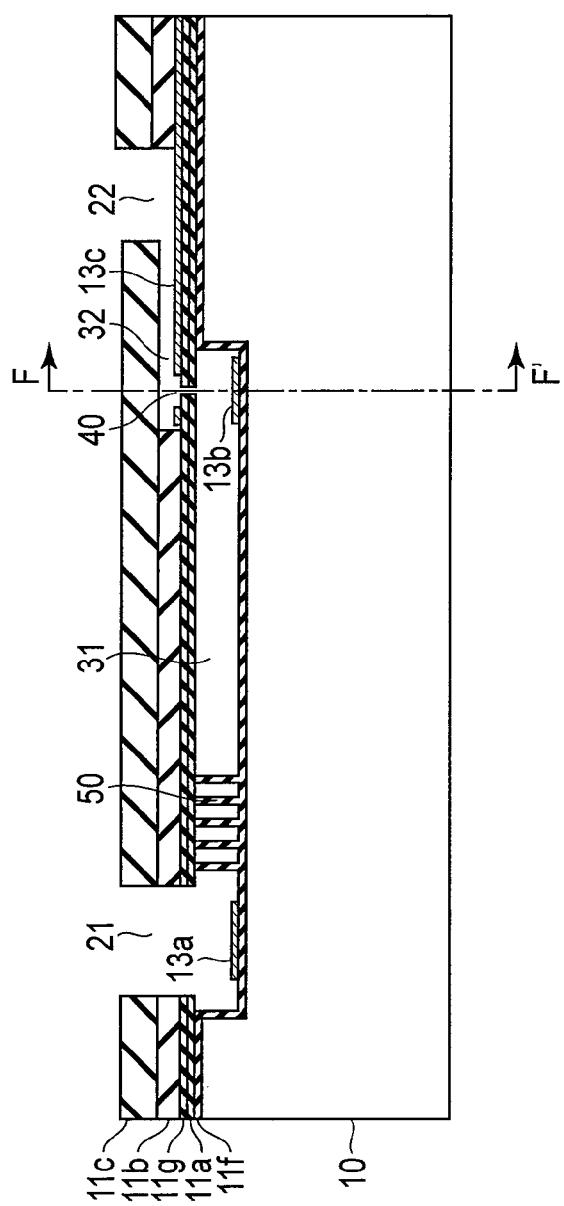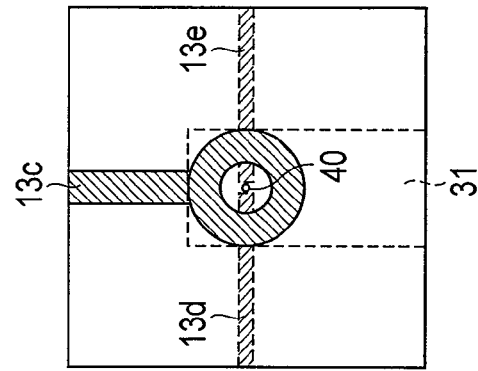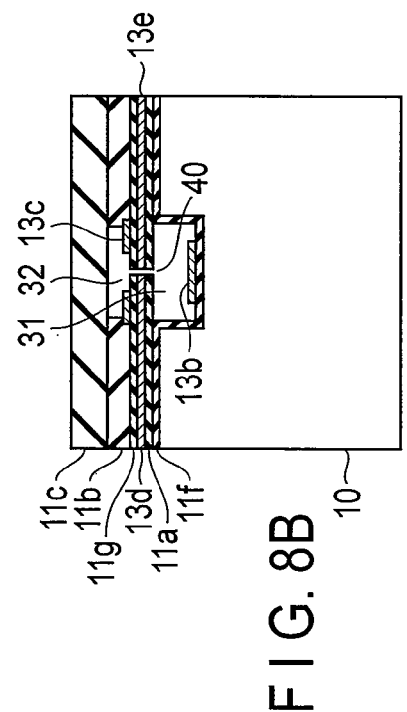

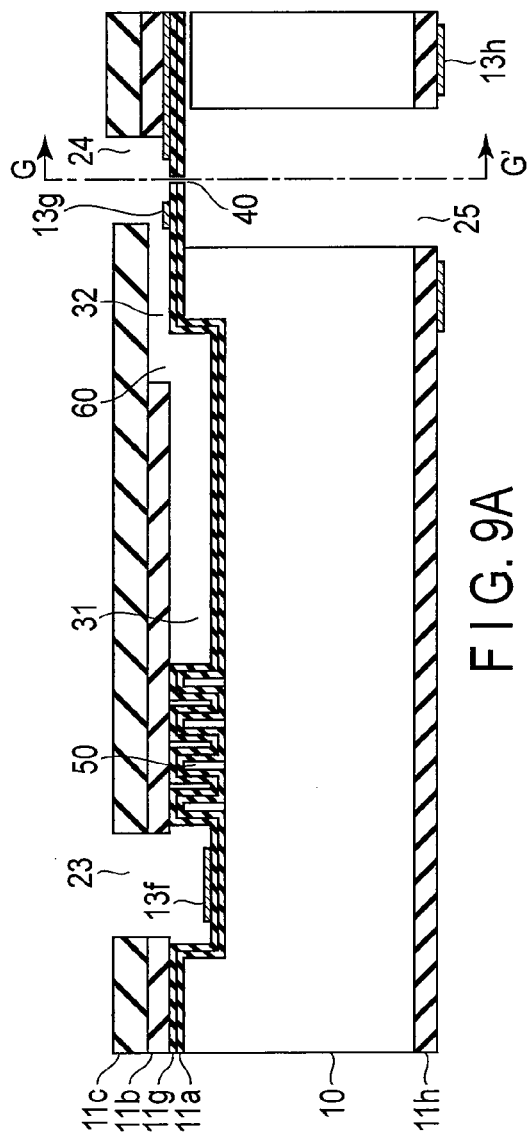
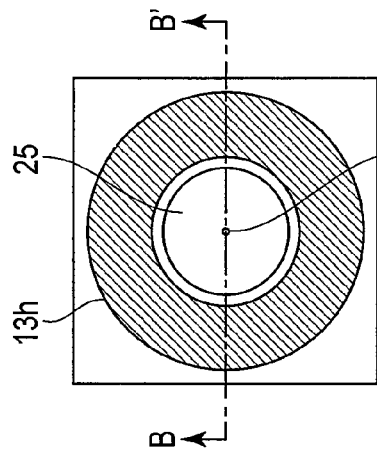
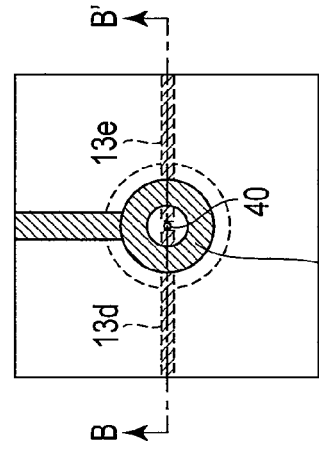
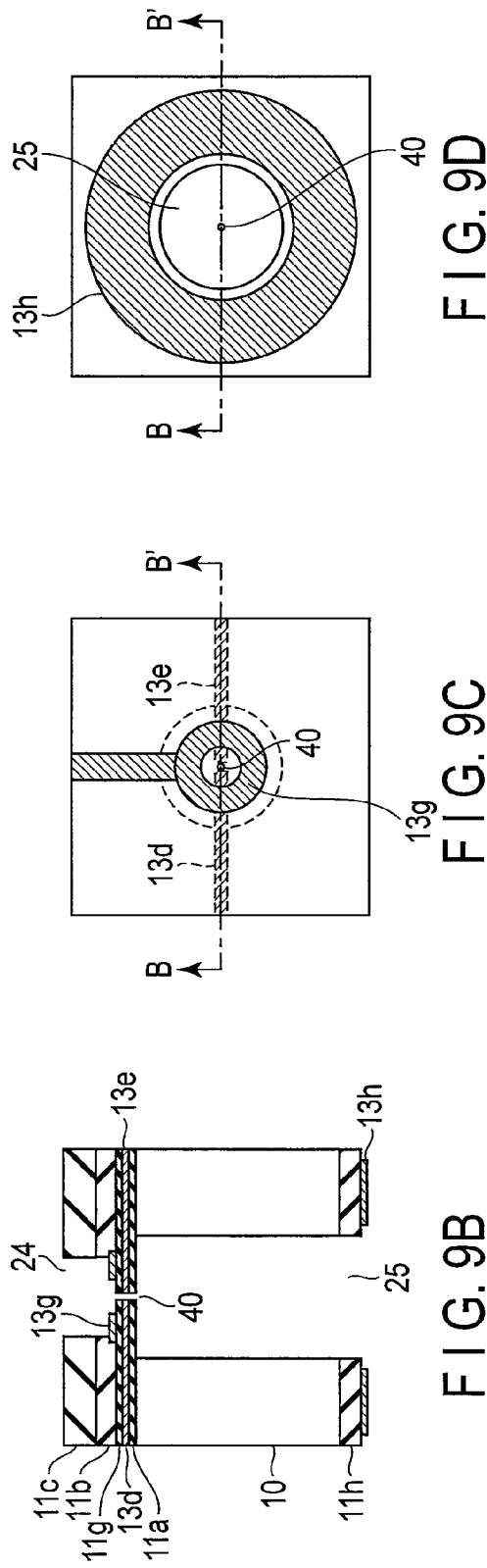

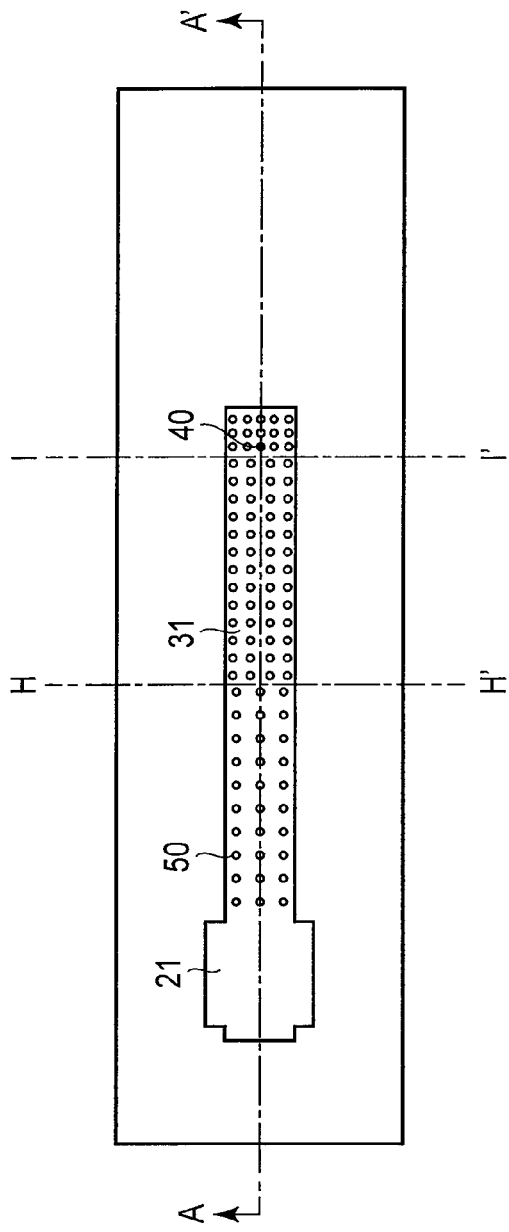
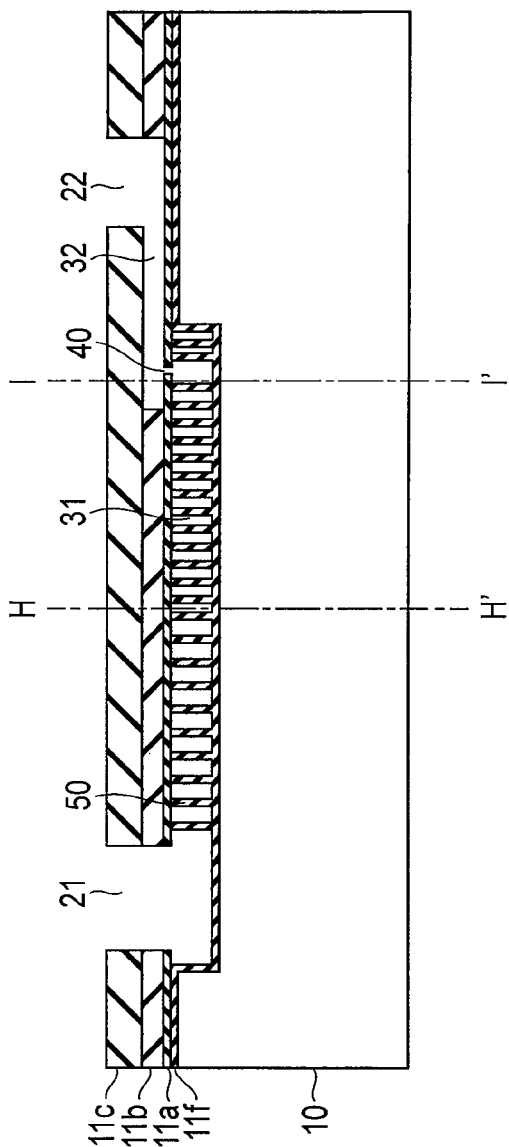
FIG. 10A
FIG. 10B

SEMICONDUCTOR ANALYSIS MICROCHIP AND METHOD OF MANUFACTURING THE SAME

CROSS-REFERENCE TO RELATED APPLICATIONS

This application is based upon and claims the benefit of priority from Japanese Patent Application No. 2013-045393, filed Mar. 7, 2013, the entire contents of which are incorporated herein by reference.

FIELD

Embodiments described herein relate generally to a semiconductor analysis microchip configured to detect a fine particle sample and a method of manufacturing the same.

BACKGROUND

In the fields of biotechnologies or health cares, analysis microchips in which microfluidic device such as micro flow channels and detection systems are integrated are attracting attention. These analysis microchips are mainly made of glass substrates. In many cases, flow channels formed in the glass substrate is capped by bonding a cover glass or the like. As sample detection techniques, laser beam scattering detection and fluorescence detection is often utilized.

However, when the glass substrate is used, to form a microstructure is difficult. Additionally, since the lid of the flow channel needs to be formed by bonding the substrate, mass production is difficult. It is therefore difficult to reduce the cost. Furthermore, there is a problem that providing a laser beam irradiation system or a fluorescence analysis system makes the analysis equipment bulky.

BRIEF DESCRIPTION OF THE DRAWINGS

FIG. 5A is a plan view showing the schematic arrangement of a semiconductor analysis microchip according to the third embodiment;

FIG. 5B is a sectional view showing the schematic arrangement of the semiconductor analysis microchip according to the third embodiment;

FIGS. 8A and 8B are sectional views showing the schematic arrangement of a semiconductor analysis microchip according to the fifth embodiment;

FIG. 8C is a plan view showing the schematic arrangement of the semiconductor analysis microchip according to the fifth embodiment;

FIGS. 9A and 9B are sectional views showing the schematic arrangement of another example of the semiconductor analysis microchip according to the fifth embodiment;

FIGS. 9C and 9D are plan views showing the schematic arrangement of another example of the semiconductor analysis microchip according to the fifth embodiment;

FIG. 10A is a plan view showing the schematic arrangement of a semiconductor analysis microchip according to the sixth embodiment;

FIG. 10B is a sectional view showing the schematic arrangement of the semiconductor analysis microchip according to the sixth embodiment;

DETAILED DESCRIPTION

In general, according to one embodiment, a semiconductor analysis microchip configured to detect a fine particle in a sample liquid, comprising: a semiconductor substrate; a first flow channel provided in the semiconductor substrate, into which the sample liquid is introduced; and a pore provided in the first flow channel and configured for the fine particle in the sample liquid to pass.

The semiconductor analysis microchip according to the embodiment has small flow channels and fine particle detection systems which are integrated on a semiconductor substrate. And the semiconductor analysis microchip detects fine particles by observing a variation of ion current flowing via a pore formed in the flow channel. A sample liquid (a suspension of fine particles to be detected) is introduced to the sample introduction port (inlet) of the flow channel, and then fills the flow channel. When one of the fine particles goes through the pore, the ion current variation occurs.

In the semiconductor analysis microchip according to the embodiment, a semiconductor such as Si is used as a substrate, the semiconductor fabrication process of is applied, and the flow channel is capped without using bonding. These enable considerable size reduction, mass production and inexpensive manufacturing of an analysis microchip. Using the microchip, it is possible to detect a fine particle of the sample with high sensitivity, because the detection method is based on observing a change of the ion current caused when the fine particle goes through the pore. In addition, since the electrical detection method is used, the device size can be much smaller than a device for optical detection.

The embodiments of the present invention will be described with reference to the accompanying drawings. Though the descriptions will be made here by exemplifying several specific materials and arrangements, the embodiments are not limited to those to be explained below, and can be practiced by any materials and arrangements having the same functions.

First Embodiment

Figure 1A:
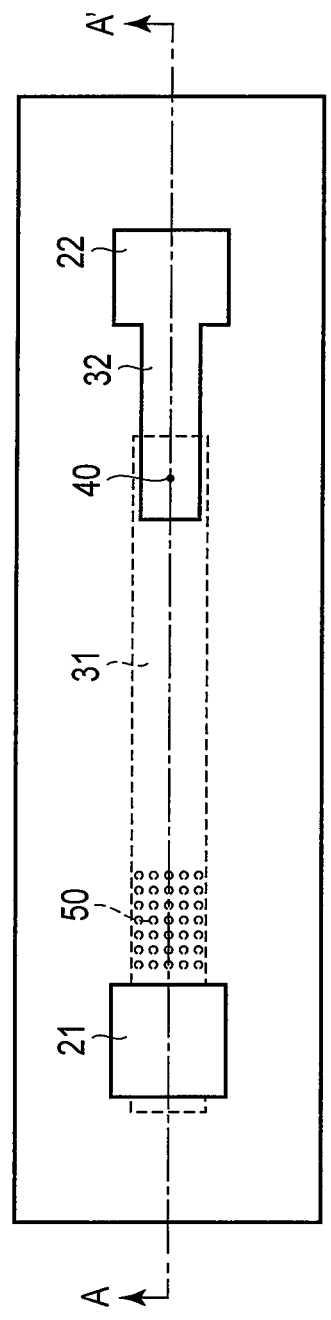
FIG. 1A is a plan view showing the schematic arrangement of a semiconductor analysis microchip according to the first embodiment.
Figure 1B:
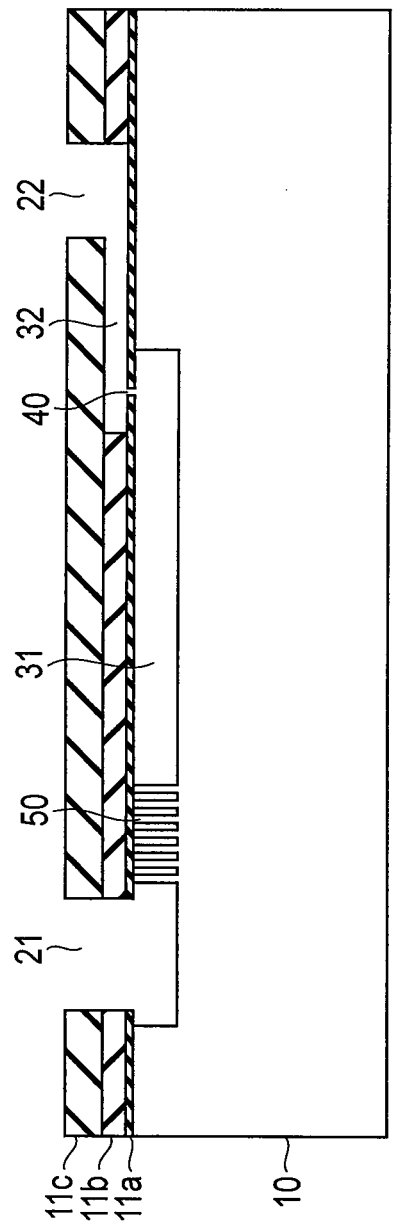
FIG. 1B is a sectional view showing the schematic arrangement of the semiconductor analysis microchip according to the first embodiment.

FIG. 1A is a plan view schematically arrangement of a semiconductor analysis microchip according to the first embodiment. FIG. 1B is a sectional view taken along line A-A' in FIG. 1A. The uppermost surface shown in FIG. 1A indicates the interface between stacked films 11b and 11c in FIG. 1B, that is, a state in which the stacked film 11c is removed.

In the analysis microchip according to this embodiment, an insulating film 11a, an insulating film 11b, and an insulating film 11c are stacked on a semiconductor substrate 10. As the semiconductor substrate 10, for example, a Si substrate is used, as described above. However, another substrate processable like Si, for example, a Ge substrate or a SiC substrate can also be used. The following passages describe the case that the semiconductor substrate 10 is a Si substrate. The insulating films 11a, 11b and 11c can be dielectric films of $SiO_2$, $Si_3N_4$, $Al_2O_3$, or the like or a polymer material such as polyimide. On the surface of the Si substrate 10, a first flow channel 31 is formed with a depth of, for example, 2 μm and connected to an introduction opening (inlet) 21 for a sample liquid. On the side of the inlet 21 of the first flow channel 31, a columnar structure array (pillar array) 50, which is extending from the bottom surface to the upper surface of the flow channel 31, is formed.

The insulating film 11a is formed so as to cap the first flow channel 31. A pore 40 is formed in a part of the insulating film 11a. In the insulating film 11b, the inlet 21, a discharge opening (outlet) 22 for the sample liquid, and a second flow channel 32 are formed. The insulating film 11c is formed so as to cap the second flow channel 32. The inlet 21 and the outlet 22 are formed at parts of the insulating film 11c. The pore 40 is arranged so as a portion of the upper surface of the first flow channel 31 to communicate with a portion of the bottom surface of the second flow channel 32. The first flow channel 31 and the second flow channel 32 are spatially connected through the pore 40.

The opening size of the pore 40 is slightly larger than the sizes of a to-be-detected fine particle (the maximum diameter of a virus, bacterium, or pollen grain, or a composite particle formed by coupling them with some other particle). More specifically, the pore 40 is made to be larger than the outer diameter of the to-be-detected fine particle by 5% or more so that the fine particle can go through the pore by liquid compression, electrophoresis, or the like. In addition, the opening size of the pore 40 can be decided in consideration of the ease for the to-be-detected fine particle to go through and the detection sensitivity of an ion current variation which is described later, and then, the opening size of the pore 40 is set, for example, from 1.5 to 5 times as large as the outer diameter of the to-be-detected fine particle.

In the analysis microchip having the above-described arrangement, after injecting a sample liquid, which contains to-be-detected fine particles, to the inlet 21, the sample liquid flows into the first flow channel 31 by capillarity and then reaches the pore 40. As the liquid to contain the to-be-detected fine particles (sample), a conductive liquid, for example, an electrolyte solution such as a KCl solution or various kinds of buffer solutions such as a buffer solution of Tris-ethylenediaminetetraacetic acid (TE) and phosphate-buffered saline (PBS) can be used. After that, the second flow channel 32 is filled with the conductive liquid containing no sample fine particle. The fine particles in the sample liquid moves in the first flow channel 31 as the sample liquid flows in the first flow channel 31 by capillarity. In this state, if needed, by inserting electrodes such as metal wires into the inlet 21 and the outlet 22, and by applying a voltage between the electrodes, the sample fine particles may be forced to migrate by means of electrophoresis.

Next, inserting electrodes (for example, metal wires) into the inlet 21 and the outlet 22 and applying a voltage between them, an ion current flowing between the electrodes via the pore 40 is observed. When an insulating fine particle is electrophoresed due to the electric field between the electrodes and goes through the pore 40, it electrically shields a portion of the opening of the pore 40. For this reason, the electrical resistance in the ion current path in the pore 40 increases, and the ion current decreases. Reversely, when the fine particle is conductive and its electron affinity hardly forms a potential barrier to the sample liquid, an increase in the ion current may be observed. Observing the ion current variation, detection of the passage of the fine particle through the pore 40 is made possible.

As shown in FIGS. 1A and 1B, the columnar structure array 50 (referred to be nanopillars hereinafter) extending from the bottom surface of the flow channel 31 to the upper surface of the flow channel 31 is arranged in the first flow channel 31 at an appropriate pillar interval. The nanopillars 50 can trap unnecessary particles having large sizes and get only fine particles having small sizes through to the downstream side of the first flow channel 31. For example, to detect a virus having a size of about 100 nm, the pillar interval of the nanopillars 50 is set to 250 nm. This makes it possible to prevent large particles with the sizes of 0.5 μm or more from reaching the pore 40 and plugging up it.

In addition, the maximum sizes of the fine particles reaching the pore 40 can be made uniform by arranging the nanopillars 50 with appropriate pillar interval and array length. In this case, since the peaks of the detected ion current variations greater than a predetermined value can be calculated as parts of noise distribution, the detection accuracy can be improved. The nanopillars 50 can also be arranged in the second flow channel 32 to prevent, for example, dust backflow from the outlet 22 side. In place of the nanopillars 50, a slit-shaped flow channel array (nanowalls) or the like is also usable.

Next, in the following passage, a method of manufacturing the semiconductor analysis microchip according to the embodiment shown in FIGS. 1A and 1B will be described with reference to FIGS. 2A to 2H.

Figure 2A:
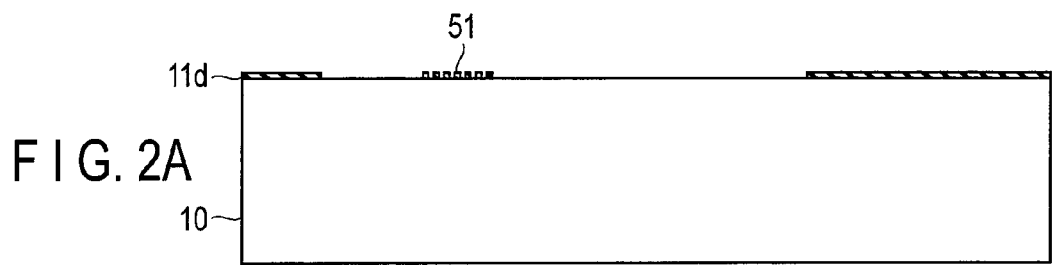
FIGS. 2A to 2H are sectional views showing steps in the manufacture of the semiconductor analysis microchip shown in FIGS. 1A and 1B.

As shown in FIG. 2A, a hard mask 51 formed from, for example, a silicon oxide film 11d is formed on an Si substrate (semiconductor substrate) 10. Specifically, after the silicon oxide film 11d is formed on the Si substrate 10 by chemical vapor deposition (CVD) or the like, the resist pattern (not shown) of the first flow channel 31 and nanopillars 50 is formed with a technique of photolithography. Then, the silicon oxide film 11d is etched using the resist as a mask, thereby forming the hard mask 51.

Figure 2B:
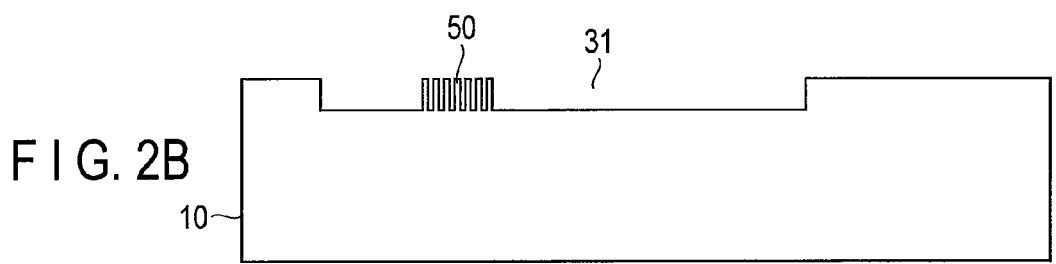

As shown in FIG. 2B, the Si substrate 10 is etched using the hard mask 51 to form the first flow channel 31 and the nanopillars 50. After etching the Si substrate, the silicon oxide film 11d can be either removed or left. The nanopillars 50 are preferably formed perpendicular to the bottom surface of the first flow channel 31. The Si substrate 10 is etched using deep reactive ion etching (RIE) such as the Bosch process.

Figure 2C:
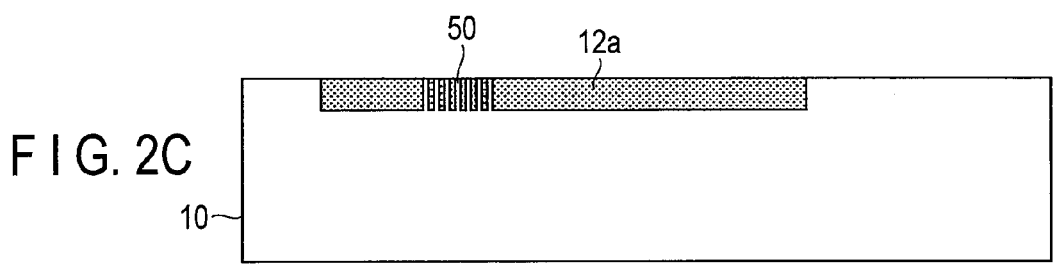

As shown in FIG. 2C, for example, a polyimide resin is formed in the portion of the first flow channel 31 as a first sacrificial layer 12a. The first sacrificial layer 12a is formed by, for example, spin-coating and hardening the precursor of a polyimide resin, followed by planarizing process of the layer using overall etching, chemical mechanical polishing (CMP), or the like until the surface of the Si substrate 10 is exposed. The surface of the Si substrate 10 can reliably be exposed by leaving the hard mask 51 in the stage of FIG. 2B and removing it in the stage of FIG. 2C. Exposing the surface of the Si substrate 10 allows the tops of the nanopillars 50 to reliably come into contact with an insulating film 11a to be formed in the next step. This can prevent unnecessary large particles from leaking from the area of nanopillars 50 through a gap formed between the nanopillars 50 and the insulating film 11a.

Figure 2D:
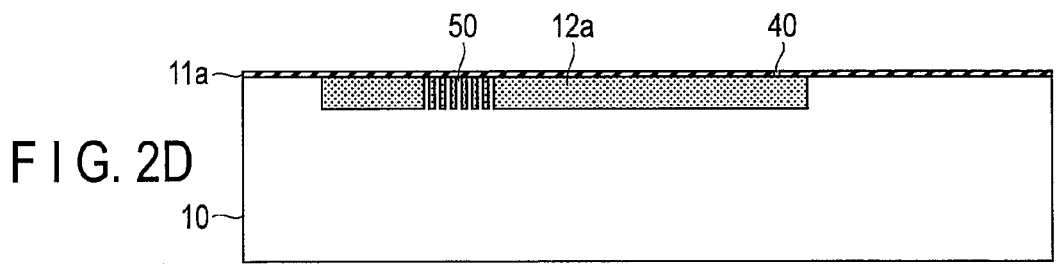

As shown in FIG. 2D, the silicon nitride film 11a is deposited by CVD. The resist pattern (not shown) of a pore 40, the position of which is aligned to the first flow channel 31, is formed by photolithography. The silicon nitride film 11a is etched using the resist as a mask, and then the pore 40 is formed. To form the resist pattern of the pore 40, electron beam (EB) lithography or ArF immersion lithography is usable.

Figure 2E:
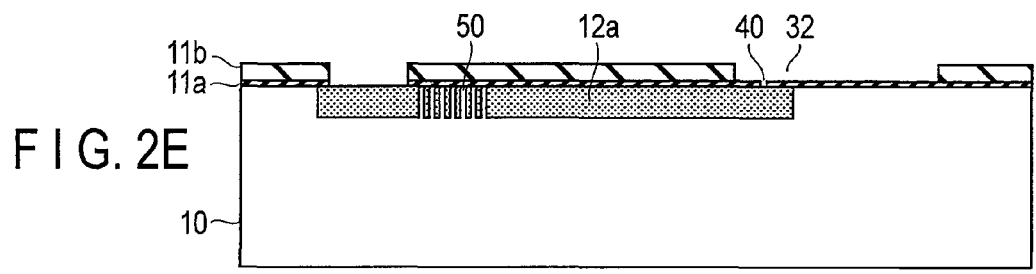

As shown in FIG. 2E, a silicon oxide film 11b is deposited by CVD. The resist pattern (not shown) of the second flow channel 32 is formed by photolithography. The silicon oxide film 11b is etched using the resist as a mask. After that, the resist is removed. The second flow channel 32 is thus formed.

Figure 2F:
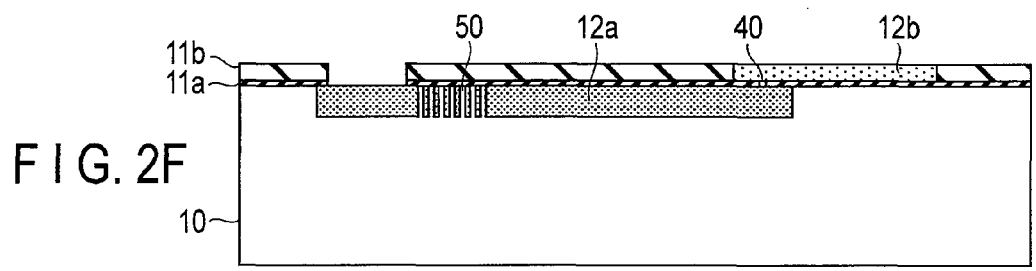

As shown in FIG. 2F, for example, a polyimide resin is formed in the portion of the second flow channel 32 as a second sacrificial layer 12b. This sacrificial layer can be formed by the same step as in FIG. 2C.

Figure 2G:
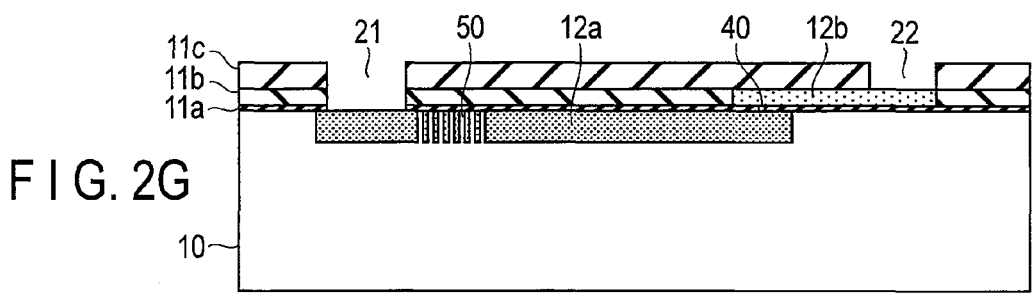

As shown in FIG. 2G, a silicon oxide film 11c is deposited by CVD. After that, the resist pattern (not shown) of the inlet 21 and the outlet 22 is formed by photolithography. The silicon oxide films 11c and 11b and the silicon nitride film 11a are sequentially etched using the resist as a mask, thereby formed the inlet 21 and the outlet 22. The resist can be removed at this stage or at the same time as sacrificial layer removal in the next step.

Figure 2H:
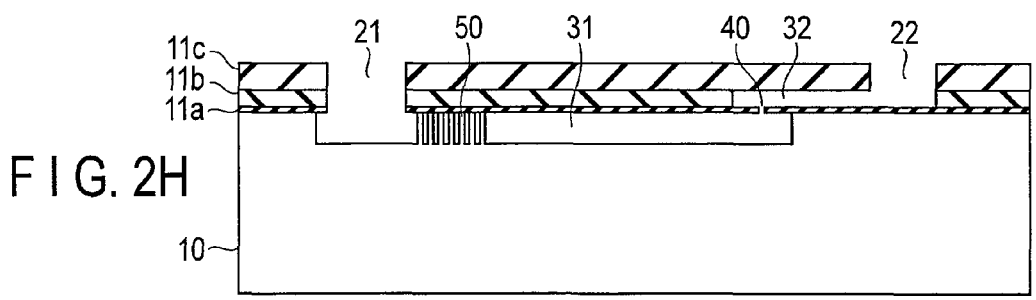

Finally, as shown in FIG. 2H, both the sacrificial layers 12a and 12b are removed using oxygen plasma ashing or the like. The sacrificial layers 12a and 12b ashed by the oxygen plasma are discharged through the openings 21 and 22.

As described above, according to this embodiment, the analysis microchip can be formed by the general semiconductor device manufacturing process using a Si substrate, and a fine particle such as a virus or a bacterium can be detected at a high sensitivity. In addition, since the microfabrication and mass production technique of the semiconductor technology is applicable, a very small analysis microchip can be manufactured at a low cost.

Second Embodiment

Figure 3A:
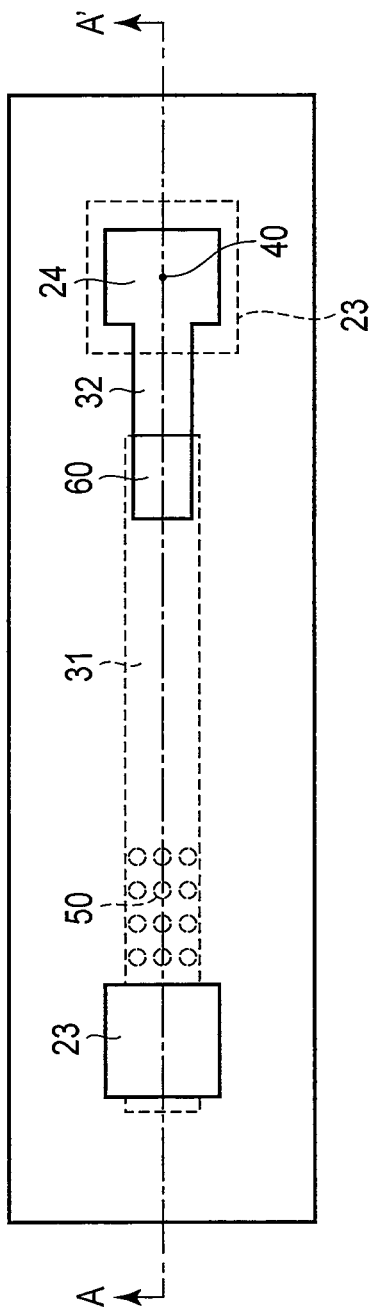
FIG. 3A is a plan view showing the schematic arrangement of a semiconductor analysis microchip according to the second embodiment.
Figure 3B:
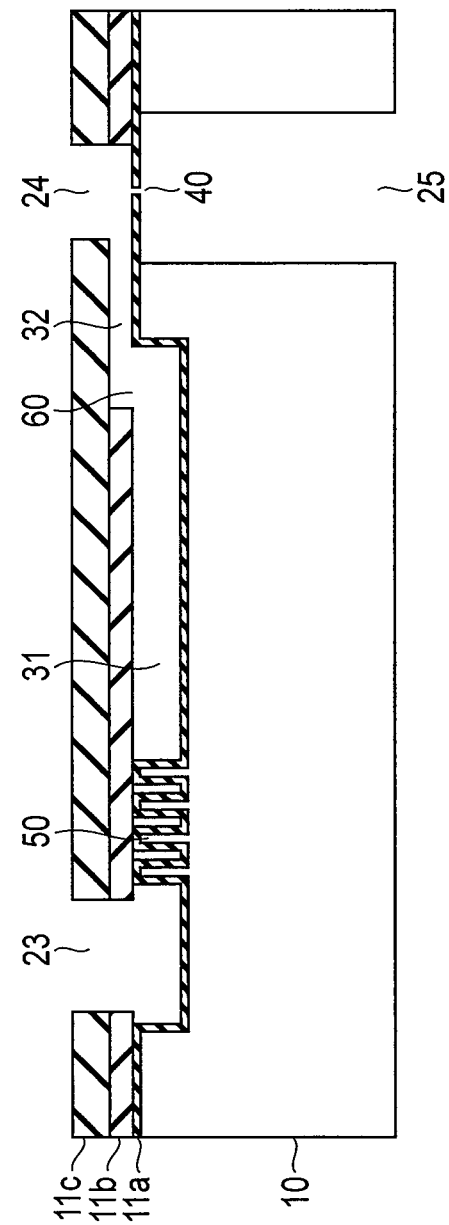
FIG. 3B is a sectional view showing the schematic arrangement of the semiconductor analysis microchip according to the second embodiment.

FIG. 3A is a plan view for explaining the schematic arrangement of a semiconductor analysis microchip according to the second embodiment. FIG. 3B is a sectional view taken along line A-A' in FIG. 3A. FIG. 3A indicates the interface between stacked films 11b and 11c in FIG. 3B, that is, a state in which the stacked film 11c is removed.

As shown in FIG. 3B, in the semiconductor analysis microchip according to the second embodiment, a pore 40 is formed in the region of a hole (referred as a lower surface opening) 25, which is created from back side of the Si substrate 10. In addition, a first flow channel 31 and a second flow channel 32 are connected so as to form one flow channel with a step in a connection region 60. The pore 40 is provided in the bottom surface of the second flow channel 32. The second flow channel 32 and the lower surface opening 25 of the Si substrate 10 are spatially connected via the pore 40.

In the semiconductor analysis microchip according to this embodiment, the sample liquid injected in the inlet 23 flows into the first flow channel 31 by capillarity, and then flows into the second flow channel 32 through the connection region 60. The lower surface opening 25 is filled with a conductive liquid containing no sample fine particle. Inserting electrodes (for example, metal wires) into the outlet 24 and the lower surface opening 25, and applying a voltage between the electrodes, an ion current between the electrodes flows through the pore 40. By observing the ion current variation caused when a fine particle goes through the pore 40, it can be detected that the fine particle goes through the pore 40 as in the first embodiment.

In addition, as in the first embodiment, arranging nanopillars 50 in the first flow channel 31 at an appropriate pillar interval, fine particles with larger sizes than the pillar interval can be trapped, and then only fine particles with smaller sizes can pass through the region of the nanopillars 50 to the downstream side. The nanopillars 50 may also be formed in the second flow channel 32. In place of the nanopillars 50, nanowalls (slit-shaped flow channel array) or the like is also usable.

A method of manufacturing the semiconductor analysis microchip according to the second embodiment will be described with reference to FIGS. 4A to 4H.

Figure 4A:
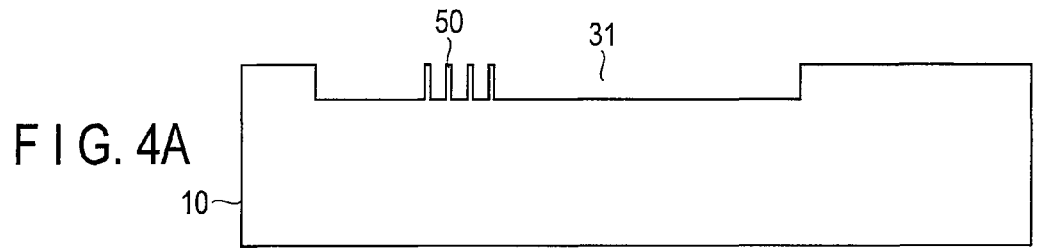
FIGS. 4A to 4H are sectional views showing steps in the manufacture of the semiconductor analysis microchip shown in FIGS. 3A and 3B.

First, the same process as in the steps of FIGS. 2A and 2B of the first embodiment is performed to form a first flow channel 31 and nanopillars 50 on an Si substrate 10, as shown in FIG. 4A.

Figure 4B:
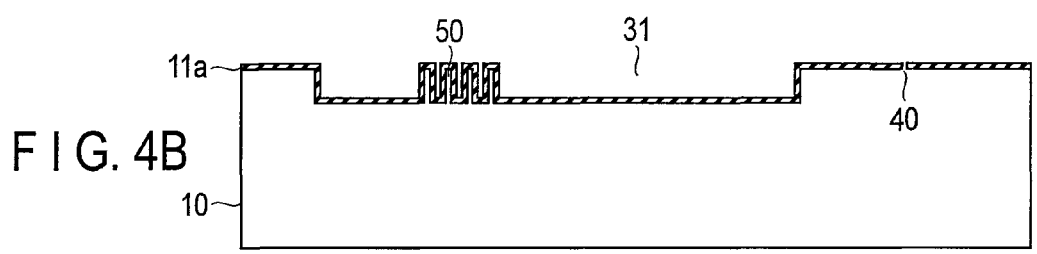

As shown in FIG. 4B, a silicon nitride film 11a is deposited by CVD. The resist pattern (not shown) of a pore is formed by photolithography on the silicon nitride film 11a. Etching is performed to form the pore 40 in the silicon nitride film 11a. After that, the resist is removed.

Figure 4C:
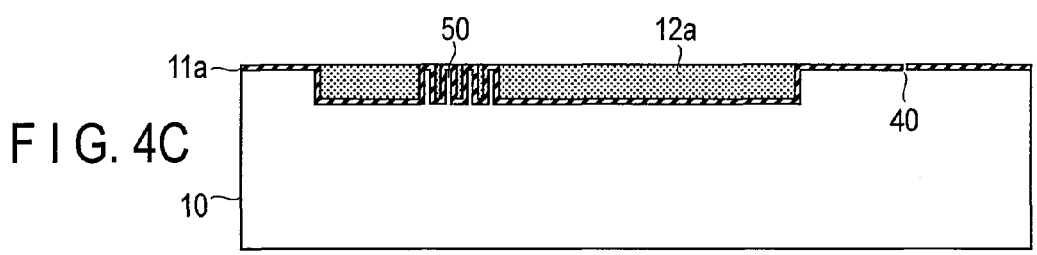
Figure 4D:
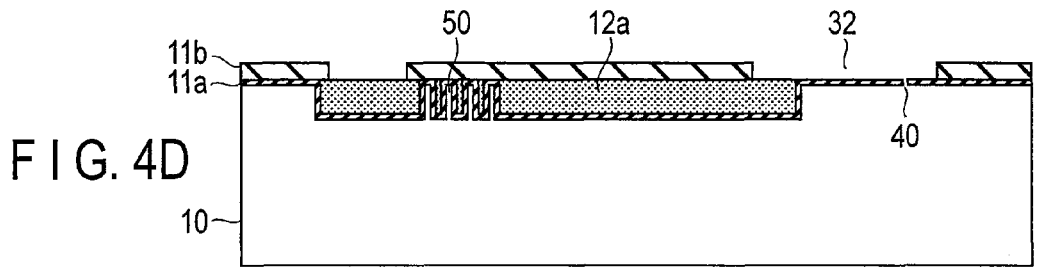

As shown in FIG. 4C, a first sacrificial layer 12a is formed in the first flow channel 31. Subsequently, as shown in FIG. 4D, a silicon oxide film 11b is deposited by CVD, and a second flow channel 32 is formed in the silicon oxide film 11b by photolithography and etching.

Figure 4E:
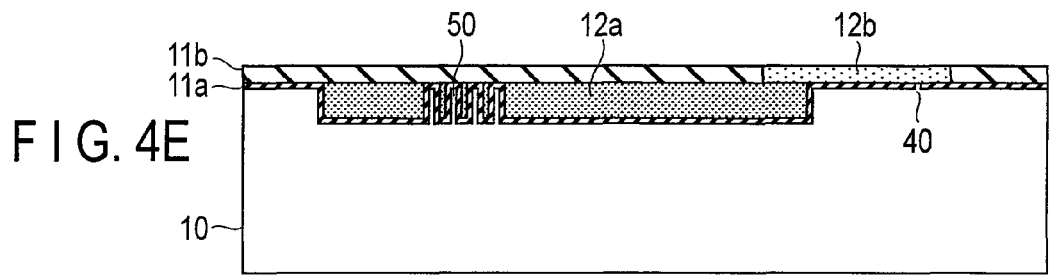
Figure 4F:
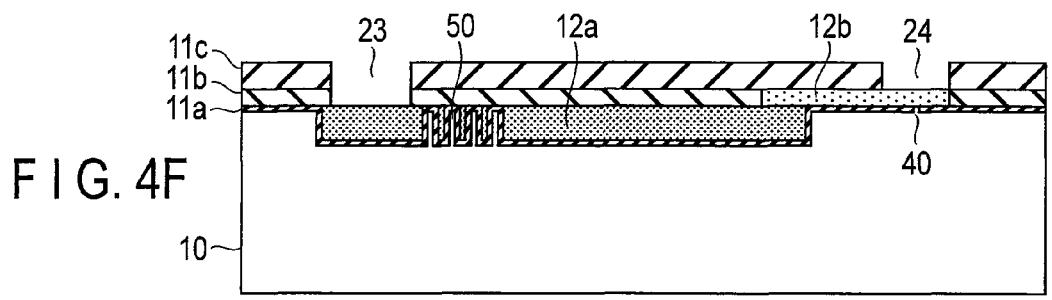

As shown in FIG. 4E, a second sacrificial layer 12b is formed in the second flow channel 32. Subsequently, as shown in FIG. 4F, a silicon oxide film 11c is deposited by CVD, and an inlet 23 and an outlet 24 are formed in the films 12a and 12b by photolithography and etching.

Figure 4G:
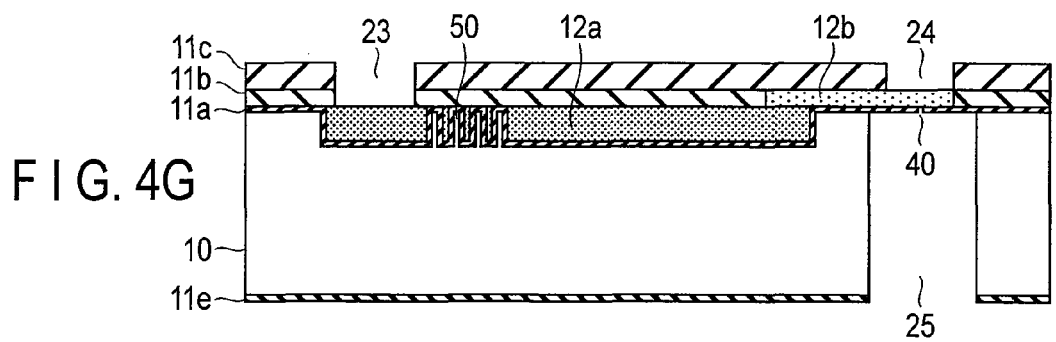

As shown in FIG. 4G, a silicon nitride film 11e is deposited on the lower surface of the Si substrate 10 by CVD. The resist pattern (not shown) of a lower surface opening 25 is formed on the lower surface by photolithography. Viewing from the lower surface of the silicon substrate 10, the resist pattern of the lower surface opening 25 is formed to overlap the pore 40. By etching the silicon nitride film 11e using the resist as a mask, the hard mask of the lower surface opening 25 is formed. Next, the Si substrate 10 is etched from the lower surface to form the lower surface opening 25. Etching of the Si substrate 10 can be executed using deep RIE such as the Bosch process. When the front surface of the silicon substrate 10 and the films formed thereon is protected by wax or the like, the etching can also be executed by wet etching using a potassium hydroxide solution or tetramethyl ammonium hydroxide (TMAH) solution. Etching of the Si substrate 10 is stopped at the film 11a where the pore 40 is formed.

Figure 4H:
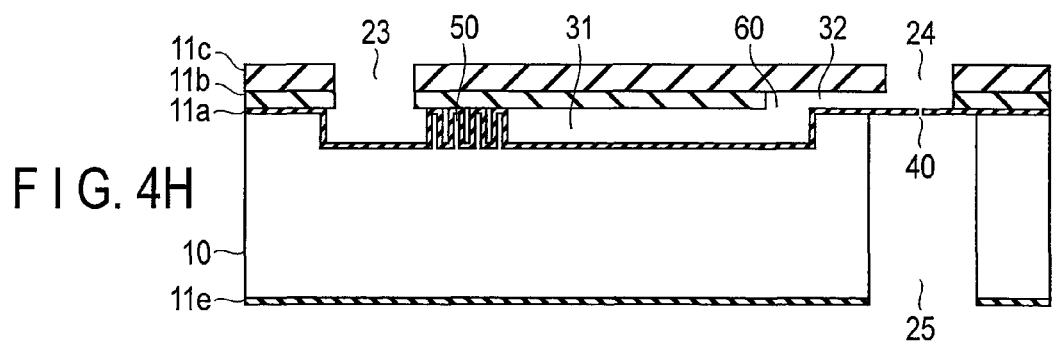

Next, as shown in FIG. 4H, the sacrificial layers 12a and 12b are removed by oxygen plasma ashing or the like.

The above-described arrangement can decrease the fluid resistance between the inlet 23 and the outlet 24, and then the flow channels 31 and 32 can more easily be filled with the sample liquid than in the first embodiment. In addition, since the distance from the electrodes (installed in the outlet 24 and the lower surface opening 25) for ion current measurement to the pore can be shorten, which makes possible to observe ion current observation at a relatively low voltage.

Third Embodiment

In the third embodiment, an oxide film is formed on the surface of a Si substrate and on the surfaces of processed structures such as a flow channel groove and nanopillars formed in the surface of the Si substrate.

FIG. 5A is a plan view for explaining the schematic arrangement of a semiconductor analysis microchip according to the third embodiment. FIG. 5B is a sectional view taken along line A-A' in FIG. 5A. FIG. 5A indicates the interface between stacked films 11b and 11c in FIG. 5B, that is, a state in which the stacked film 11c is removed.

This embodiment is different from the first embodiment in that an oxide film is formed on the surface of a Si substrate 10. That is, a silicon oxide film 11f is added to the surfaces of the Si substrate 10, a first flow channel 31, and nanopillars 50 in the first embodiment.

In the first embodiment, Si is exposed on the bottom and side surfaces of the first flow channel 31. Filling the first flow channel 31 with a sample liquid and a second flow channel 32 with a conductive liquid containing no sample fine particle, inserting electrodes (for example, metal wires) into an inlet 21 and an outlet 22, and applying a voltage, an ion current flows between the electrodes via a pore 40. At this time, since the conductive liquid is in contact with the Si surface, a leakage current may flow through the Si substrate 10 if the applied voltage is raised to several volts or more.

Therefore, in this embodiment, the silicon oxide film 11f is added to the surfaces where the sample liquid and the conductive liquid are in contact, to increase the electrical insulation. The silicon oxide film 11f is, for example, a thermal oxide film. To form the thermal oxide film 11f, a thermal oxidation process can be done just after forming the first flow channel 31 and the nanopillars 50 (FIG. 2B), that is, just before forming a sacrificial layer 12a (FIG. 2C) in the semiconductor analysis microchip manufacturing process according to the first embodiment. Although silicon oxide film deposition by CVD is also usable as the method of forming the silicon oxide film 11f, formation by thermal oxidation is preferably used because of the stability of dielectric strength.

In addition, since the $SiO_2$ surface is more hydrophilic than the Si surface, the wettability to the sample liquid and the like can be improved by forming the silicon oxide film 11f on the bottom and side surfaces of the first flow channel 31, as shown in FIGS. 5A and 5B. That is, the structure of this embodiment not only increases the electric insulation but also is a suitable structure for improving the wettability to the sample liquid.

In this embodiment, since the nanopillars 50 and the first flow channel 31 are formed in the Si substrate 10 monolithically, the surfaces of the nanopillars 50 are also oxidized in the above-described thermal oxidation process. The molar volumes of Si and $SiO_2$ are 12.06 and 27.20 $cm^3$, respectively, so when $SiO_2$ is formed by thermal oxidization of Si, the volume increases to 2.26 times. That is, when the pillar surfaces are thermally oxidized, the pillar diameter and interval change from the configuration obtained after the pillars are formed by etching the Si substrate. For this reason, if the oxidation amount for each Si pillar is uneven, the pillar diameter and interval vary, and then the size-filtering function of the nanopillars for fine particles may be impaired.

On the other hand, if thermal oxidation process is performed until all Si pillars completely turn into $SiO_2$, the diameter and interval of the pillars do not vary any more. Hence, by forming the Si pillars in a size to obtain desired-sized $SiO_2$ pillars by inverse calculation from the volume ratio of Si to $SiO_2$ and by oxidizing the Si pillars completely, the uniformity of the outer diameter and interval of pillars can easily be controlled. In addition, by designing the Si pillars such that a desired nanopillar array is obtained after the Si pillars are completely oxidized, it is possible to form thicker thermal oxide film 11f on the surface of the Si substrate 10 than the oxidation thickness of the Si pillars. This makes it possible to increase the dielectric strength of the Si substrate while suppressing variations in the array of the $SiO_2$ pillars.

As described above, according to this embodiment, it is possible to implement a semiconductor analysis microchip in which the Si substrate has a high dielectric strength, and the flow channels have excellent wettability.

Note that the arrangement and manufacturing method of this embodiment are applicable to both the first and the second embodiments, as a matter of course.

Fourth Embodiment

In the fourth embodiment, a tunnel-shaped flow channel is formed. This will be described with reference to FIGS. 6A to 6C and 7A to 7C.

Figure 6A:
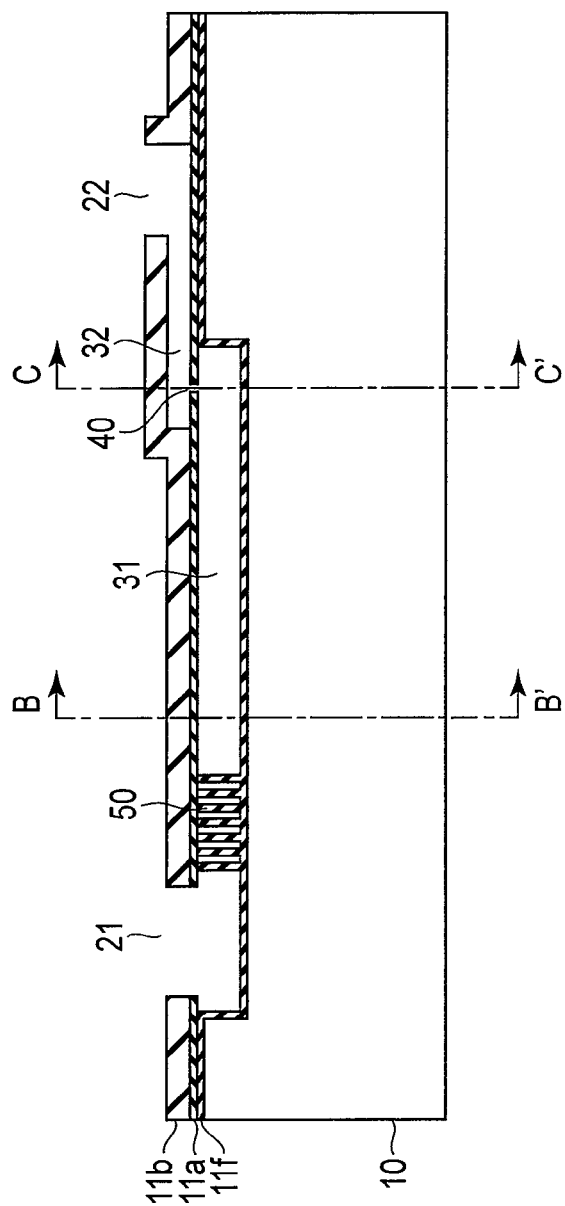
FIGS. 6A to 6C are sectional views showing the schematic arrangement of a semiconductor analysis microchip according to the fourth embodiment.
Figure 6B:
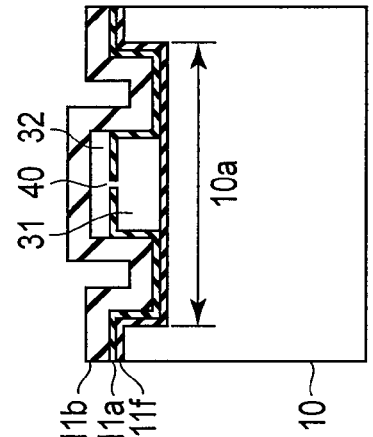
Figure 6C:
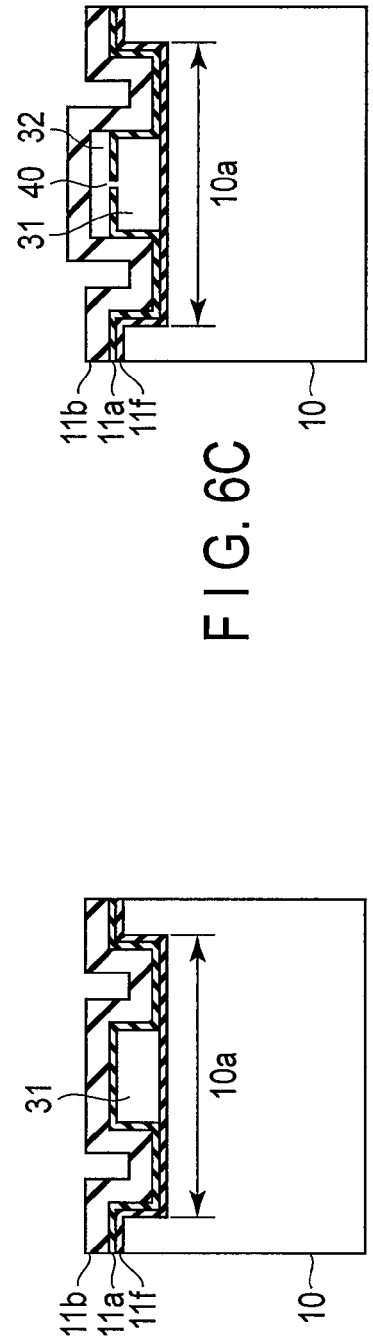

FIG. 6A is a sectional view for explaining the schematic arrangement of a semiconductor analysis microchip according to the fourth embodiment. FIG. 6B is a sectional view taken along line B-B' in FIG. 6A. FIG. 6C is a sectional view taken along line C-C' in FIG. 6A. FIGS. 6A to 6C illustrate an embodiment having a function corresponding to the first embodiment shown in FIGS. 1A and 1B in which the Si substrate has no lower surface opening, and a pore 40 is located between a first flow channel 31 and a second flow channel 32.

Figure 7A:
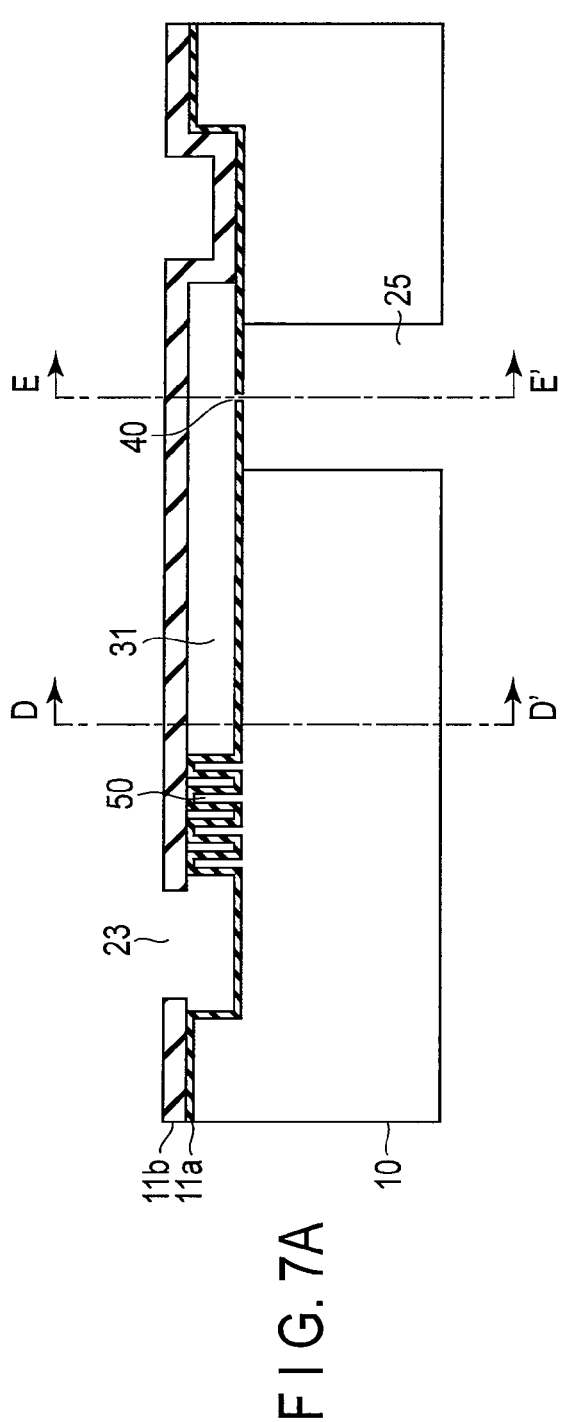
FIGS. 7A to 7C are sectional views showing the schematic arrangement of another example of the semiconductor analysis microchip according to the fourth embodiment.
Figure 7C:
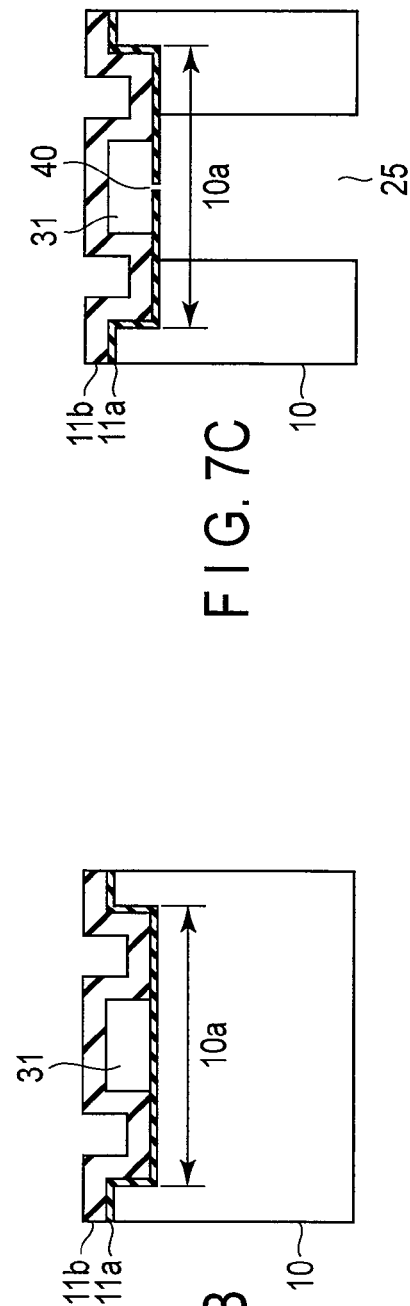
Figure 7B:
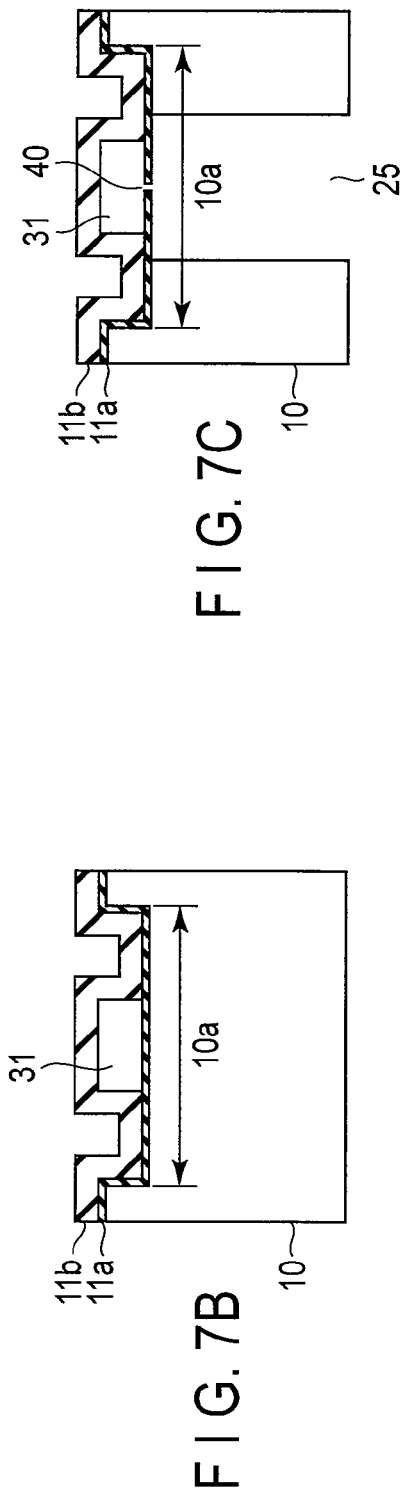

FIG. 7A is a sectional view for explaining the schematic arrangement of a semiconductor analysis microchip according to a modification of the fourth embodiment. FIG. 7B is a sectional view taken along line D-D' in FIG. 7A. FIG. 7C is a sectional view taken along line E-E' in FIG. 7A. FIGS. 7A to 7C illustrate an embodiment having a function corresponding to the second embodiment shown in FIGS. 3A and 3B in which the Si substrate has a lower surface opening, the pore 40 is formed in an insulating film 11a in contact with the Si substrate, and a lower surface opening 25 is formed under the pore 40.

As shown in FIG. 6A, in the analysis microchip of this embodiment, insulating films 11f, 11a, and 11b are stacked on a Si substrate 10. As one example, the insulating film 11f is a silicon thermal oxide film, the insulating film 11a is a silicon nitride film, and the insulating film 11b is a silicon oxide film. An engraved region 10a is formed in the Si substrate 10, as shown in FIGS. 6B and 6C. In the engraved region 10a, a hollow structure is provided between the silicon thermal oxide film 11f and the silicon nitride film 11a, as shown in FIG. 6B. This hollow structure serves as the first flow channel 31. As shown in FIG. 6C, another hollow structure is provided between the silicon nitride film 11a and the silicon oxide film 11b. This hollow structure serves as the second flow channel 32. The first flow channel 31 and the second flow channel 32 are spatially connected through the pore 40 formed in the silicon nitride film 11a.

In the semiconductor analysis microchip manufacturing method of the above-described first embodiment (FIGS. 2A to 2H), the structure of the first flow channel 31 filled with the first sacrificial layer 12a is formed by engraving the surface of the Si substrate 10, applying the material of the first sacrificial layer to the entire surface, and removing the sacrificial layer material outside the engraved portion etchback by non-masking etching or CMP. Following that, the structure of the second flow channel 32 filled with the second sacrificial layer 12b is formed by depositing and etching the silicon oxide film 11b, applying the material of the second sacrificial layer to the entire surface and applying the same process as that for the first sacrificial layer. However, in the process of burying the sacrificial layer material using etch-back or CMP, the surface height of the sacrificial layer readily differs in the engraved portion and the flat portion, and the surface planarity of the sacrificial layer is difficult to ensure.

In contrast, in this embodiment, after forming the engraved region 10a and nanopillars 50 on the surface of the Si substrate 10, a first sacrificial layer pattern narrower than the engraved region 10a is formed inside the engraved region 10a. Following that, by forming the insulating films 11a and 11b to cover the first sacrificial layer pattern and by removing the first sacrificial layer, a first tunnel-shaped flow channel can be formed. That is, the width of the engraved region 10a in the Si substrate is made to be much larger than desired width of the first flow channel 31, and the height and the width of the flow channel are determined by the thickness and the pattern width of the first sacrificial layer. Since the height, the width, and the pattern of the first flow channel can be determined only by the first sacrificial layer pattern, the first flow channel 31 can be formed at an extremely high accuracy. In addition, since the pattern and the level of the first flow channel 31 can easily be aligned to the nanopillars 50, the fabrication yield can be improved, and then the manufacturing cost can be reduced. By designing the region where the nanopillars 50 are formed wider than the width of the first flow channel, leakage from the particle filter caused by misalignment of the nanopillars 50 and the first flow channel can be prevented.

Next, after forming the insulating film 11a on the first tunnel-shaped flow channel 31, a second sacrificial layer pattern narrower than the engraved region 10a is formed so as to overlap the insulating film 11a. Following that, by forming the insulating film 11b to cover the second sacrificial layer pattern and by removing the second sacrificial layer, a second tunnel-shaped flow channel can be formed. This obviates the necessity to uniform the surface height of the sacrificial layer in the flat portion and the engraved portion of the Si substrate. That is, the semiconductor analysis microchip of this embodiment can be implemented without planarizing the sacrificial layer material. In addition, the reproducibility of intra- and inter-wafer process can be improved.

As the manufacturing step of the embodiment shown in FIGS. 6A to 6C, a thermal oxide film 11f is formed on the surface after forming the engraved region 10a on the surface of a Si substrate 10. Next, a first sacrificial layer pattern narrower than the engraved region 10a is formed followed by a silicon nitride film 11a deposition thereon. Next, a pore 40 is formed in the silicon nitride film 11a, and a second sacrificial layer pattern is formed. A silicon oxide film 11b is deposited, and an inlet 21 and an outlet 22 are formed by etching. After that, removing the sacrificial layer material is removed by oxygen ashing or the like, a first flow channel 31 and a second flow channel 32 which have a tunnel shape are obtained.

As a modification of the fourth embodiment, FIGS. 6A to 6C can be applied to the embodiment shown in FIGS. 3A and 3B as well as the embodiment shown in FIGS. 1A and 1B. That is, the first flow channel 31 and the second flow channel 32 of the embodiment shown in FIGS. 3A and 3B can be formed in tunnel shape narrower than the engraved region 10a of the Si substrate 10, as shown in FIGS. 6A to 6C. The second flow channel 32 can be connected to the lower surface opening 25 through the pore 40, as in FIGS. 3A and 3B. This makes possible to have both the effect of the embodiment shown in FIGS. 3A and 3B and the effect of the embodiment shown in FIGS. 6A to 6C.

In addition, as shown in FIGS. 7A to 7C, a structure in which the pore 40 is formed in the bottom surface of the tunnel-shaped first flow channel 31 and connected to the lower surface opening 25 can also be implemented. In the structure shown in FIGS. 7A to 7C, though the pore 40 needs to be formed in the engraved region of the Si substrate, the process of forming the second sacrificial layer for the second flow channel 32 can be omitted. This is effective as an inexpensively manufacturable arrangement when the pore 40 has a relatively large diameter.

Fifth Embodiment

In the fifth embodiment, the electrodes used for electrophoresis or fine particle detection are integrated on a semiconductor analysis microchip. This will be described with reference to FIGS. 8A to 8C and FIGS. 9A to 9D.

FIG. 8A is a sectional view of the semiconductor analysis microchip according to this embodiment. This corresponds to an embodiment that the electrodes used for electrophoresis or fine particle detection are integrated in the above-described first embodiment. FIG. 8B is a sectional view taken along line F-F' in FIG. 8A. FIG. 8C is a plan view near a pore 40 and indicates a state in which stacked films 11b and 11c in FIG. 8A are removed. FIG. 9A is a sectional view of a semiconductor analysis microchip according to a modification of the embodiment. This corresponds to an embodiment that the electrodes used for electrophoresis or fine particle detection are integrates in the above-described second embodiment. FIG. 9B is a sectional view taken along line G-G' in FIG. 9A. FIG. 9C is a plan view near the pore 40. FIG. 9D is a bottom view near a lower surface opening 25. FIG. 9C indicates a state in which the stacked films 11b and 11c in FIG. 9A are removed.

FIG. 8A shows an embodiment that the electrodes are integrated in the embodiment shown in FIGS. 7A to 7C. Electrodes 13a and 13b are provided in the region of an inlet 21 and the region of the pore 40, respectively, on the bottom surface of the first flow channel 31, or silicon oxide film 11f. A ring-shaped electrode 13c is provided around the pore 40 on the silicon nitride film 11a. Electrophoresis of fine particles in the first flow channel 31 can be controlled by applying a voltage to the electrodes 13a and 13b. Control of electrophoresis of fine particles to the pore 40 or observation of an ion current through the pore 40 can be done by applying a voltage to the electrodes 13b and 13c. The electrophoresis of fine particles can be caused even by applying a voltage to the electrodes 13*a* and 13*c*. In this case, observation of the ion current through the pore 40 is also possible simultaneously. Ion current observation using the electrodes 13*b* and 13*c* can improve the detection sensitivity because the electrical resistance or noise superimposition in the flow channel can be suppressed.

FIG. 9A is a modification illustrating the case that the electrodes are integrated in the embodiment shown in FIGS. 4A to 4H. A silicon nitride film 11*g* is further provided in the embodiment shown in FIGS. 3A and 3B. Electrodes 13*f* and 13*g* are provided in the region of an inlet 23 and around the pore 40, respectively, on the silicon nitride film 11*g*. An insulating film 11*h* is provided on the lower surface of the Si substrate 10. A ring-shaped electrode 13*h* is provided around the lower surface opening 25. The insulating film 11*h* is provided for insulation between the Si substrate 10 and the electrode 13*h*. For example, the silicon nitride film 11*e* (FIG. 4G) used in the second embodiment to form the lower surface opening 25 can be used as the insulating film 11*h*.

In the embodiment shown in FIG. 9A, electrophoresis of fine particles in the first flow channel 31 can be controlled by applying a voltage to the electrodes 13*f* and 13*g*. Control of electrophoresis of fine particles to the pore 40 or observation of an ion current through the pore 40 can be done by applying a voltage to the electrodes 13*g* and 13*h*. The electrophoresis of fine particles can be caused even by applying a voltage to the electrodes 13*f* and 13*h*. In this case, observation of the ion current through the pore 40 is also possible. Ion current observation using the electrodes 13*g* and 13*h* can improve the detection sensitivity because the electrical resistance or noise superimposition in the flow channel can be suppressed.

As described above, according to this embodiment, electrophoresis of fine particles or observation of the ion current through the pore 40 can be done without preparing external electrodes. It is therefore possible to reduce the size of analysis equipment using the semiconductor analysis microchip and to increase its sensitivity.

In the above-described embodiment, electrodes for ion current observation placed apart from the pore 40 to some extent have been described. However, opposite electrodes may be arranged on both sides of the pore 40 for direct observation of the fine particle passing through the pore 40. In FIGS. 8B and 9B, electrodes 13*d* and 13*e* are provided along with the electrodes 13*b*, 13*c*, 13*g*, and 13*h*. The electrodes 13*d* and 13*e* are formed between the silicon nitride films 11*a* and 11*g* and arranged to face each other across the pore 40. The electrodes 13*d* and 13*e* are used to apply an electric field in traverse direction of the opening plane of the pore 40.

When a fine particle in the sample liquid goes through the pore 40, the impedance between the electrodes 13*d* and 13*e* changes. This is because the ion current or inter-electrode capacitance between the electrodes 13*d* and 13*e* changes. This is also because when the diameter of the pore 40 is sufficiently small and the gaps between the passing fine particle and the electrodes 13*d* and 13*e* and are nm order, the tunnel current flowing through the electrode 13*d*, the fine particle, and the electrode 13*e* changes. The passage of the fine particle through the pore 40 and the properties of the fine particle that has passed through the pore 40 can be detected by observing the change in the current or capacitance between the electrodes 13*d* and 13*e*. With this detection method, the base sequence of deoxyribonucleic acid (DNA) can be read especially when the opening diameter of the pore 40 is several nm. Therefore, not only the function of simply detecting the passage or the size of a fine particle but also a new function can be imparted to the semiconductor analysis microchip.

As described above, according to this embodiment, various kinds of electrodes can be integrated in the first to fourth embodiments, and ion current change observation or electrophoresis control can be done without using external electrodes. In addition, the physical properties of a fine particle can also be detected by providing opposite electrodes near the pore 40.

Sixth Embodiment

In the sixth embodiment, nanopillars are arranged all over the flow channel, and the flow of a sample liquid into the flow channel is prompted using the surface tension (capillarity) acting on the liquid among the nanopillars. This will be described with reference to FIGS. 10A and 10B.

FIG. 10A is a plan view of a semiconductor analysis microchip according to the sixth embodiment. FIG. 10B is a sectional view taken along line A-A' in FIG. 10A. FIG. 10A shows the surface of an insulating film 11*f*, that is, the exposed surfaces of nanopillars without stacked films 11*a*, 11*b*, and 11*c*. Application to the semiconductor analysis microchip structure according to the third embodiment will be exemplified here.

FIG. 10A shows the state immediately after a first flow channel 31 and nanopillars 50 are formed on a Si substrate 10. The method of forming the first flow channel 31 and the nanopillars 50 is the same as in the third embodiment. However, the nanopillars 50 are not arranged only on the side of an inlet 21 in the first flow channel 31 but arranged all over the first flow channel 31.

In the semiconductor analysis microchip formed in this way, the sample liquid injected in the inlet 21 flows into the first flow channel 31 by capillarity. In addition, since the nanopillars 50 are arranged all over the first flow channel 31, the surface area of the first flow channel 31 becomes much larger than that of the first flow channel without nanopillars, and hence the effect that the capillarity is enhanced is obtained, which results in that the sample liquid sequentially flow to the nanopillars on the downstream side. In addition, since the first flow channel 31 is covered with the silicon thermal oxide film 11*f* with high hydrophilicity, the wettability of the flow channel is improved as compared to a case in which the nanopillars 50 are not arranged all over the flow channel. For this reason, in this embodiment, it is made easy for the sample liquid to flow in the first flow channel 31, so the sample testing time can be shortened and testing errors caused by, for example, bubble inclusion can easily be prevented.

As shown in FIG. 10A, the nanopillar interval is made smaller on the right side of line H-H', that is, on the downstream side of the first flow channel 31 than that on the upstream side of line H-H'. This makes it possible to trap, at boundary H-H', fine particles whose size is larger than the nanopillar interval on the downstream side of line H-H'. Similarly, the nanopillar interval is made further smaller on the right side of line I-I' than that between line H-H' and line I-I'. This makes it possible to trap, at boundary I-I', fine particles whose size is larger than the nanopillar interval on the downstream side of boundary I-I' and further fine particles with smaller size to go to the right side.

In this case, selective size filtering is possible so that unnecessary large particles are trapped at boundary H-H', fine particles to be detected are collected at boundary I-I', and unnecessary small particles are sent to the right side of boundary I-I'. This makes it possible to collect fine particles of a desired size selectively and to guide them to the pore 40. Hence, in this embodiment, the detection sensitivity is dramatically improved by selective collection of to-be-detected fine particles at high concentration and then raising the probability that the to-be-detected fine particles go through the pore 40.

Note that although the structure in which the nanopillars 50 are arranged all over the first flow channel 31 has been described above, the nanopillars 50 may be arranged all over a second flow channel 32. Moreover, the nanopillars may be arranged all over both the first flow channel 31 and the second flow channel 32.

Seventh Embodiment

In the seventh embodiment, a liquid absorber is added outside a semiconductor analysis microchip according to the first to sixth embodiments so as to continuously cause the capillarity of a sample liquid, that is, to keep the sample liquid's flow caused by the surface tension. This embodiment will be described with reference to FIGS. 11A and 11B.

Figure 11A:
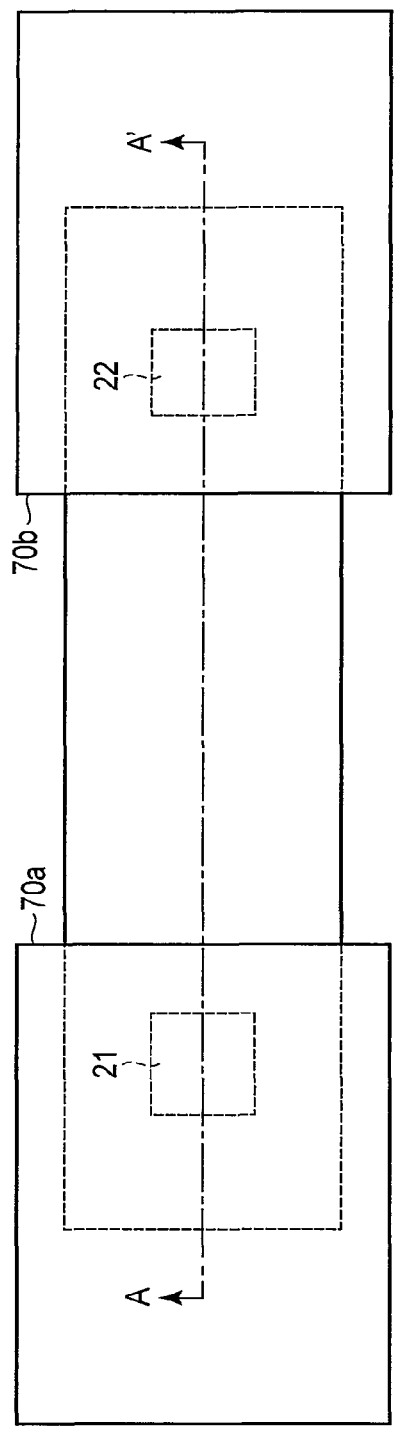
FIG. 11A is a plan view showing the schematic arrangement of a semiconductor analysis microchip according to the seventh embodiment.
Figure 11B:
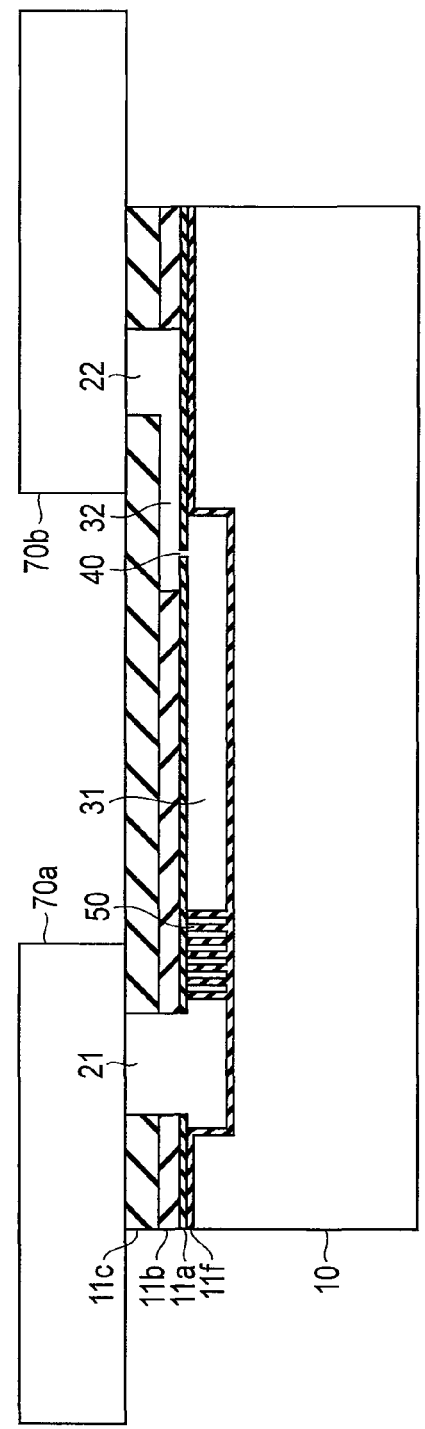
FIG. 11B is a sectional view showing the schematic arrangement of the semiconductor analysis microchip according to the seventh embodiment.

FIG. 11A is a plan view of a semiconductor analysis microchip according to the seventh embodiment. FIG. 11B is a sectional view taken along line A-A' in FIG. 11A. Application to the semiconductor analysis microchip structure according to the third embodiment will be exemplified here. In FIG. 11A, only a stacked film 11c on the top surface, an inlet 21, an outlet 22, and absorbers 70 (70a and 70b) capable of absorbing a sample liquid are depicted for the sake of simplicity. The absorbers 70 are arranged in contact with the stacked film 11c, as shown in FIG. 11B.

Generally, sample liquid injection into the analysis microchip is done using a micropipetter or the like, and its drop amount is about 10 to 10,000 mL. To receive this amount of sample liquid, for example, a depth of 100 μm and an area of 100 mm² are necessary. To integrate this huge reception region on the semiconductor analysis microchip, a chip size much larger than the size of the functional portions integrated in an analysis chip is necessary. This leads to an immense cost increase. In addition, the concentration of fine particles in the sample liquid is generally low. To detect a lot of fine particles, an enormous amount of sample liquid needs to be injected. To enable this, a huge sample liquid reception region is required.

In the semiconductor analysis microchip of this embodiment, instead of integrating a very large sample liquid inlet, a sufficiently large absorber 70a is placed outside the analysis chip, and the sample liquid is dropped on the absorber 70a and injected into a first flow channel 31. The sample liquid discharged from the outlet 22 can be absorbed by the absorber 70b. These make it possible to inject and discharge the sample liquid in a larger volume than the sample liquid volume stored in the analysis chip.

As described above, in this embodiment, a large amount of sample liquid can be handled using a very small analysis chip. The cost can largely be reduced by integrating the functional portions of the semiconductor analysis microchip in a minimum area.

Additionally, in this embodiment, the pillar array can be arranged all over the inlet 21 or the outlet 22. This can increase the contact area between the absorber 70a and the inlet 21 of the sample liquid and that between the outlet 22 and the absorber 70b. In this case, injection and discharge of the sample liquid can be done more efficiently.

Modifications

Note that the present invention is not limited to the above-described embodiments.

In the above-described embodiments, a Si substrate is used as the semiconductor substrate. However, not only Si but also any other semiconductor material can be used if it can be processed with the normal semiconductor manufacturing process. In the above-described embodiments, pillar structures (pillars) are used to trap particles having a large size. However, the nanopillars may be omitted when the size of the detection-target fine particle is not limited, or the size of the detection-target fine particle is predetermined.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A semiconductor analysis microchip configured to detect a fine particle in a sample liquid, comprising:
    a semiconductor substrate;
    a first flow channel provided between a first insulating film and a second insulating film in the semiconductor substrate, into which the sample liquid is introduced, the first flow channel including a groove provided in the semiconductor substrate, the first insulating film being in direct contact with a bottom surface and side surfaces of the groove, and the second insulating film putting a lid on at least part of the groove;
    a second flow channel provided above the first flow channel, the second flow channel including a third insulating film at least partially stacked on the second insulating film; and
    a pore provided in the second insulating film between the first flow channel and the second flow channel to allow the fine particle in the sample liquid to pass therethrough, wherein the pore is not provided in the first insulating film.

2. The microchip according to claim 1, wherein the first insulating film comprises a silicon oxide film.

3. The microchip according to claim 1, wherein the second insulating film comprises a silicon nitride film.

4. The microchip according to claim 1, wherein the third insulating film comprises a silicon oxide film.

5. The microchip according to claim 1, wherein a thickness of the semiconductor substrate is greater than a thickness of the second insulating film.

6. A semiconductor analysis microchip configured to detect a fine particle in a sample liquid, comprising:
    a semiconductor substrate;
    a first flow channel provided in the semiconductor substrate, into which the sample liquid is introduced, the first flow channel including a groove provided in the semiconductor substrate, and a first insulating film putting a lid on at least part of the groove;
    a second flow channel provided above the first flow channel, the second flow channel including a second insulating film at least partially stacked on the first insulating film and having a groove pattern, and a third insulating film putting a lid on at least part of the groove pattern of the second insulating film; and
    a pore provided in the first insulating film between the first flow channel and the second flow channel to allow the fine particle in the sample liquid to pass therethrough, wherein the pore is not provided in the second insulating film.

7. The microchip according to claim 6, wherein the second flow channel is provided between the first insulating film and the third insulating film.

8. The microchip according to claim 1, wherein the first insulating film and the second insulating film are of different materials.

9. The microchip according to claim 6, further comprising a liquid inlet which penetrates the first insulating film, the second insulating film, and the third insulating film.

* * * * *